United States Patent [19]

Goldsmith, III et al.

[11] Patent Number: 5,139,510

[45] Date of Patent: Aug. 18, 1992

[54] NASAL PACKING DEVICE

[75] Inventors: Manning M. Goldsmith, III, Savannah, Ga.; George C. Robertson, Ponte Vedra Beach, Fla.

[73] Assignee: Xomed-Treace Inc., Jacksonville, Fla.

[21] Appl. No.: 659,012

[22] Filed: Feb. 22, 1991

[51] Int. Cl.$^5$ ............................................. A61M 31/00
[52] U.S. Cl. ..................................................... 606/196
[58] Field of Search .................................. 606/191–196; 604/93–97, 99, 101, 104, 106; 128/656–658, 207.18, 207.15, DIG. 20

[56] References Cited

U.S. PATENT DOCUMENTS

| | | | |
|---|---|---|---|
| 3,516,407 | 6/1970 | Ruggero | 606/196 |
| 3,774,596 | 11/1973 | Cook | 604/96 |
| 3,903,893 | 9/1975 | Schur | 606/196 |
| 4,850,969 | 7/1989 | Jackson | 604/96 |

Primary Examiner—C. Fred Rosenbaum
Assistant Examiner—M. Mendez
Attorney, Agent, or Firm—Rodman & Rodman

[57] ABSTRACT

The nasal packing device includes a splint portion, an airway member secured to the splint portion and a flexible expandable membrane secured to the airway member. An inflation chamber is thus defined between the flexible expandable membrane and the airway member. Under this arrangement, expansion of the membrane is in a direction away from the airway member enabling the membrane to provide a substantially uniform pressure against the splint portion and against any portions of the nose which the membrane comes into contact with. A uniform compressive force provided by the expandable membrane is thus attainable within the nasal passageway to arrest intranasal bleeding, while the splint supports the septum and the airway member allows nasal breathing.

20 Claims, 2 Drawing Sheets

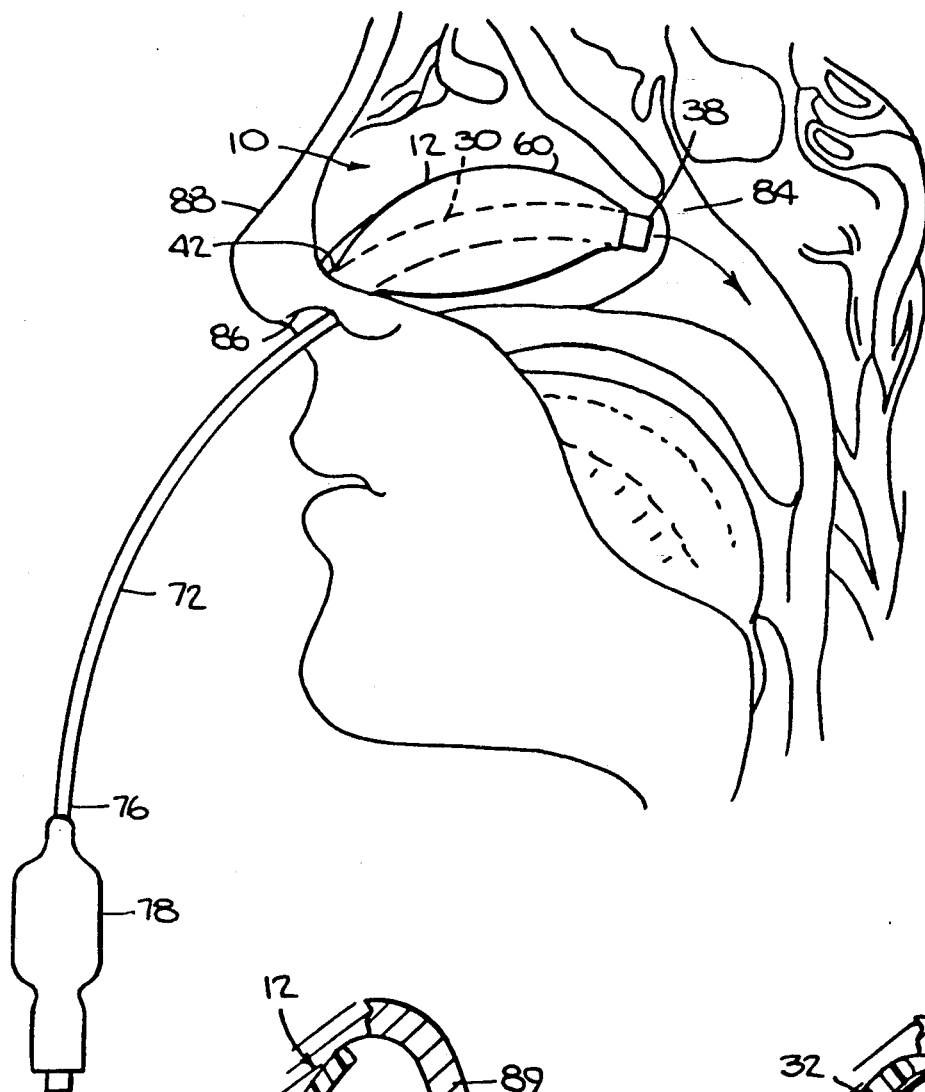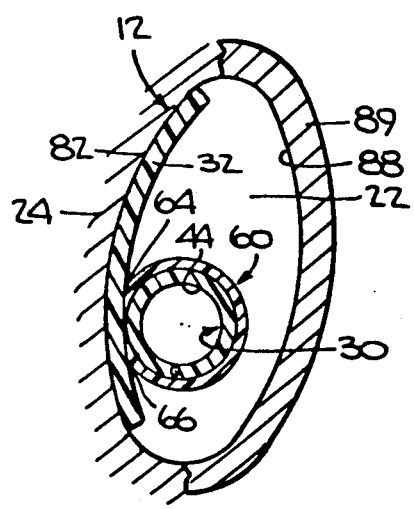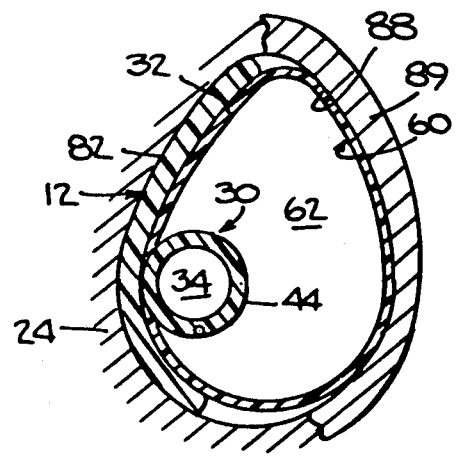

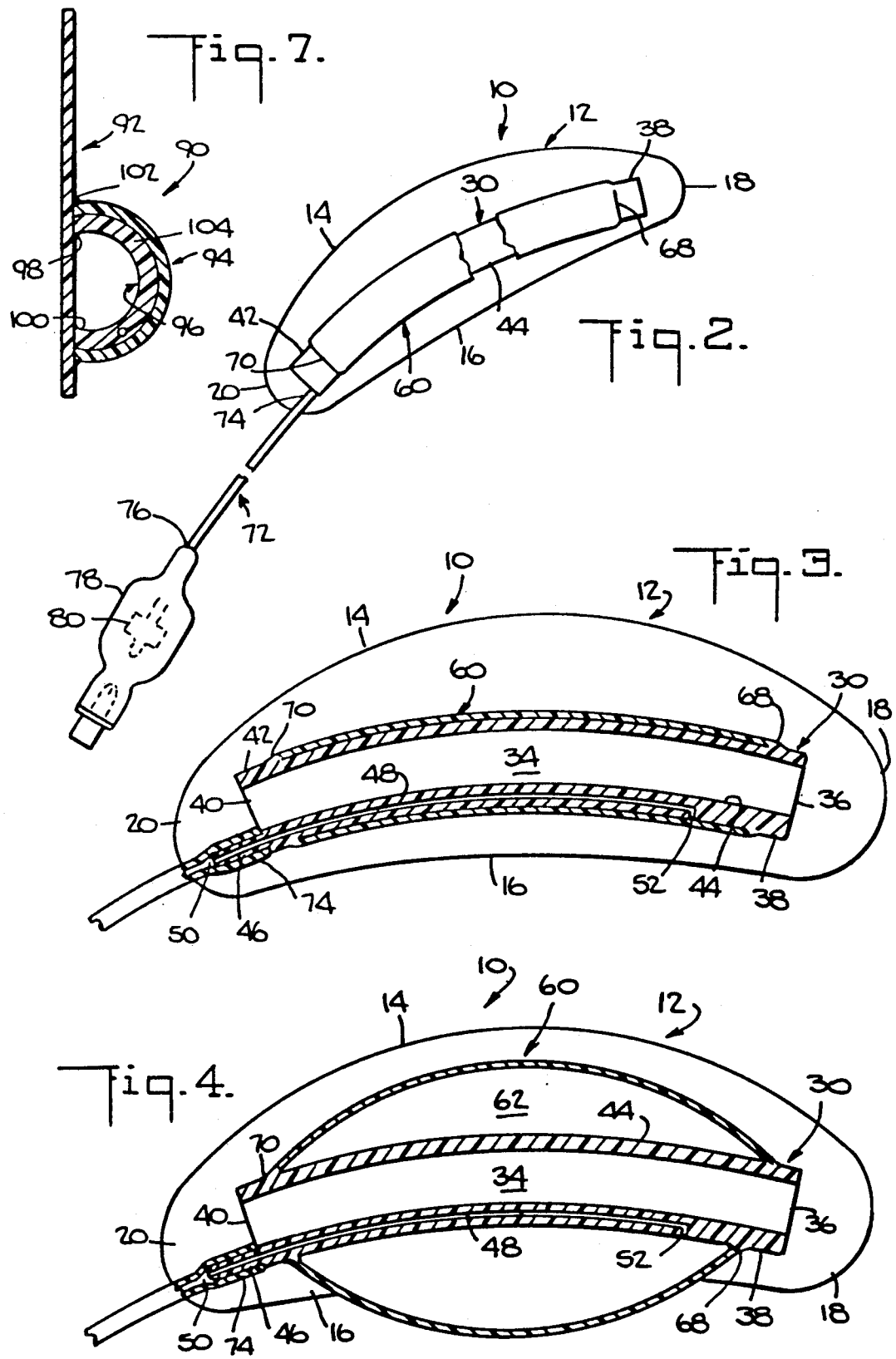

NASAL PACKING DEVICE

BACKGROUND OF THE INVENTION

This invention is directed to nasal packing devices and more particularly to a novel nasal packing device that provides septal support, permits nasal breathing and controls nasal bleeding.

Nasal surgery, such as the restructuring or repair of the septum, often involves use of post-operative support devices that stabilize the septum and thus aid the healing process.

In addition to the need for septal support during the healing process, there is also a need to control or arrest intranasal bleeding and allow nasal breathing to take place.

Known devices which accomplish one or more of the desired functions of septal support, control of intranasal bleeding and facilitation of nasal breathing include absorbent sponge nasal packing devices as sold under the trademark Naso-Tamp ® Expandable Nasal Packing Sponge. The absorbent sponge packing material helps control nasal bleeding but does not provide optimum septal support or permit nasal breathing.

A dual cuff inflatable catheter for controlling nasal bleeding and permitting nasal breathing, sold under the trademark Epistat TM Nasal Catheter, although providing control of intranasal bleeding and permitting nasal breathing, also does not provide optimum support of the septum.

Nasal septal splints which include an airway and a septal support, such as sold under the trademark Doyle TM Airway Splint, provide a desired support for the septum but do not provide optimum control of intranasal bleeding and are thus generally used with packing material such as tampons of the type sold under the trademark Merocel ® Nasal Tampons. Oftentimes, the splint and tampon are installed separately which can be an inconvenience to the physician and a discomfort to the patient.

U.S. Pat. No. 4,606,346 to Berg et al. for intranasal device, discloses a plastic septal splint having an airway tube and a balloon device joined to a surface of the splint. The tube and the balloon are spaced from each other. The splint thus provides support for the septum, while the airway tube permits nasal breathing and the balloon helps control intranasal bleeding. When the splint is inserted into the nasal passage and the balloon is inflated, portions of such balloon can expand against the airway tube and against the surface of the splint. Balloon pressure is thus transmitted to the septal splint by direct contact with the balloon surface and by balloon contact against the airway tube. However, where the balloon contacts or crosses the airway tube a pressure difference may occur resulting in nonuniform distribution of balloon pressure along the splint. Balloon expansion may also result in a partial or total blockage of the airway passage.

It is thus desirable to provide a nasal packing device that supports the septum, permits nasal breathing, controls nasal bleeding and provides substantially uniform pressure distribution along the support septum and along the intranasal tissue within the nasal passage.

OBJECTS AND SUMMARY OF THE INVENTION

Among the several objects of the invention may be noted the provision of a novel nasal packing device, a novel nasal packing device that provides septal support, permits nasal breathing and controls nasal bleeding, a novel nasal packing device that employs an inflatable member and an airway member conjoined together and joined to a septal support, a novel nasal packing device which provides optimum support for a septum and optimum control of intranasal bleeding while permitting breathing during the postoperative healing period, a novel nasal packing device which provides a substantially uniform distribution of pressure within the nasal passageway while permitting optimum support of the septum, and a novel method of packing a nasal passageway.

Other objects and features of the invention will be in part apparent and in part pointed out hereinafter.

In accordance with one embodiment of the invention, the nasal packing device includes a flexible nonexpandable splint portion shaped to conform to the septal portion of the nose. An airflow member is joined to an obverse surface of the splint portion and a flexible expandable membrane is joined to a peripheral surface of the air flow member. An inflation chamber is thus defined between the peripheral surface of the air flow member and the flexible expandable membrane.

The air flow member provides a passageway for flow of air from a vestibular portion of the nose to the nasopharyngeal opening. The air flow member also includes a lumen for inflating the inflation chamber, which lumen communicates with an inflation tube including an inflation bulb having an inflation valve.

If desired, the inflation lumen can be dispensed with and an inflation member can be fitted directly to the expandable membrane.

The nasal packing device is installed in a nasal passageway with the splint portion placed adjacent the septal portion of the nose. Inflation of the expandable membrane causes the inflation chamber to expand away from the air flow member and exert a pressure against the lateral crus of the nose as well as the splint portion. Since the inflatable member expands away from the airway member there is no interference of the membrane with the airway member and substantially uniform pressure can be applied along the interior surface of the nasal passageway.

The air flow member can be of tubular shape or of semi-tubular shape and the flexible expandable membrane can be secured entirely to the surface of the air flow member or partially secured to the air flow member and the splint.

In this manner, a substantially uniform pressure is supplied against the splint portion as well as the lateral crus portion of the nose, thereby providing a desired support for the nose as well as arresting nasal bleeding following septal surgery.

The invention accordingly comprises the constructions and method hereinafter described, the scope of the invention being indicated in the claims.

DESCRIPTION OF THE DRAWINGS

In the accompanying drawings,

FIG. 1 is a simplified schematic pictorial view of a nasal packing device incorporating one embodiment of the invention, in an installed position in the nasal passage;

FIG. 2 is a simplified plan view thereof;

FIG. 3 is an enlarged simplified plan view thereof, partly shown in longitudinal section;

FIG. 4 is a view similar to FIG. 3 showing the inflatable member in an inflated condition;

FIG. 5 is a lateral sectional view thereof after installation in a nasal passage, wherein the inflatable member is in an unexpanded condition;

FIG. 6 is a view similar to FIG. 5 showing the inflatable member in an expanded condition; and, FIG. 7 is a simplified lateral sectional view of another embodiment of the invention.

Corresponding reference characters indicate corresponding parts throughout the several views of the drawings.

DETAILED DESCRIPTION OF THE INVENTION

A nasal packing device incorporating one embodiment of the invention is generally indicated by the reference number 10 in FIG. 1.

Referring to FIGS. 2–4, the nasal packing device 10 includes a flexible nonexpandable flap member or splint portion 12, which can be formed of a suitable biocompatible material such as soft silicone. The splint portion 12, which can be approximately 1 mm. thick, is of generally elongated shape having opposite elongated edge portions 14 and 16, the edge portion 14 having a greater degree of curvature than the edge portion 16. The splint portion 12 also includes a curved distal end portion 18 and an opposite curved proximal end portion 20.

The shape and curvature of the splint portion 12 are predetermined to facilitate disposition of the splint in a nasal passageway 22 (FIG. 5) such that the splint portion 12 bears against a septal portion 24 of the nasal structure.

An airway member such as a tube 30, having a generally circular cross section, and formed of a suitable biocompatible material such as silicone, is bonded to an obverse surface 32 of the splint portion 12. The tube 30, which can have an outside radius of 4.77 mm. or outside diameter of 9.54 mm., is bonded to the splint portion 12 in any suitable known manner as by using an adhesive or a curing process.

Referring to FIG. 3, the tube 30 includes an airway passage 34 with an opening 36 at a distal end 38 and an opposite opening 40 at a proximal end 42.

The tube 30 is slightly curved from the proximal end 42 to the distal end 38 and generally follows the curvature of the edge portion 14. The tube 30 includes a generally cylindrical wall portion 44 approximately 1 mm. thick that is formed with an extension fitting 46 at the proximal end 42. A lumen 48 is provided in the wall portion 44 and the fitting 46. The lumen 48 has a inlet opening 50 at a free end of the fitting 46 and an outlet opening 52 in the wall portion 44 a predetermined distance from the distal end 38.

A flexible expandable membrane 60 is joined to the wall portion 44 to form a leak-tight inflation chamber 62 (FIG. 4) between the membrane 60 and the wall portion 44. The membrane includes elongated longitudinal edge portions 64 and 66 as most clearly shown in FIG. 5, joined to the wall portion 44 at or near the junction between the tube 30 and the splint portion 12. The flexible expandable membrane 60 further includes lateral edge portions 68 and 70, as most clearly shown in FIG. 2, joined to the wall portion 44 proximate the respective distal and proximal end portions 38 and 42. Under this arrangement, the inflation chamber 62 is rendered substantially leak tight at the edges 64, 66, 68 and 70. The membrane 60 can be formed of silicone approximately 0.25 mm. thick, with general overall dimensions of approximately 10×53 mm.

An inflation tube 72 includes one end portion 74 joined to the fitting 46 and an opposite end portion 76 joined to a suitable known inflation bulb 78 containing a suitable known control valve 80 that is normally closed.

In using the nasal packing device 10, after septal surgery for example, the splint portion 12 is disposed in the nasal passageway 22 as shown in FIG. 5, with the membrane 60 in an unexpanded condition. The splint portion 12 is positioned against the septum 24 such that the obverse surface 32 faces into the nasal passageway 22 and a reverse surface 82 is in contact with the septum 24. The distal end portion 38 of the tube 30 is directed toward the nasopharyngeal opening 84 (FIG. 1) and the proximal end portion 42 of the tube 30 extends toward the nasal vestibule 86. Under this arrangement, the inflation tube 72 extends away from the nose and the membrane 60 is entirely recessed within the nasal passageway 22.

The inflation bulb 78 is actuated in any suitable known manner as by squeezing to inflate the inflation chamber 62 thereby causing the expandable membrane 60 to expand against the splint portion 12 and into surface-to-surface contact with the interior surface 88 of the lateral crus 89 of the nose as shown in FIG. 6.

The membrane 60 upon inflation of the inflation chamber 62 substantially conforms to the inner surfaces 88 of the nose as well as the obverse surface 32 of the splint portion 12. Since the membrane 60 does not expand against the tube 30 but essentially expands away from the tube 30, the tube 30 does not obstruct expansion of the membrane 60. In this manner, a predetermined, substantially uniform pressure is provided by the membrane 60 against all interior surfaces of the nose, either through the splint portion 12 or by direct contact with the interior surface 88 of the nasal wall portions as shown in FIG. 6.

It will also be noted that since the membrane 60 expands away from the tube 30, the possibility that such membrane will obstruct or impede functioning of the tube 30 is substantially minimized. Nasal breathing through the airway passage 34 of the tube 30 is thus assured.

To maintain the inflation chamber 62 in its inflated condition after the inflation process is completed, the inflation tube 72 can be pinched or otherwise secured at the end portion 74 in any suitable known manner, with the remaining portion of the inflation tube 72 being cut and removed.

When it is desired to deflate the inflation chamber 62, the distal end portion 74 of the inflation tube 72 can be cut upstream of the pinch point to thereby release the trapped air. With the inflation chamber 62 in an uninflated condition, the membrane 60 collapses against the tube 30 and the splint portion 12 can remain in place for any additional time necessary to provide support of the septal portion 24. Eventual removal of the nasal packing device 10 can be easily accomplished in any suitable known manner.

Another embodiment of the nasal packing device is generally indicated by the reference number 90 in FIG. 7. The nasal packing device 90 includes a splint portion 92 similar to the splint portion 12, a flexible expandable membrane 94 similar to the flexible expandable membrane 60 and an air flow member 96 having a generally C-shape in cross section.

The air flow member 96 corresponds to the air flow member 30 and includes edge portions 98 and 100 bonded to an obverse surface 102 of the splint portion 92. The membrane 94 can be bonded to the wall portion 104 of the air flow member 96 in a manner similar to that previously described for bonding the membrane 60 to the wall portion 44 of the tube member 30.

Although not shown, a lumen similar to the inflation lumen 48 is formed in the wall portion 104 of the air flow member 96. The nasal packing device 90 is used in a manner similar to that previously described for the nasal packing device 10.

As will be apparent to those skilled in the art, whether the airway member is of tubular shape as in the packing device 10 or of C-shape as in the packing device 90, expansion of the flexible expandable membrane is in a direction away from the respective air flow members and thus does not impede the function of the air flow member or otherwise block the passage of air through the air flow member.

Some advantages of the present invention evident from the foregoing description include a nasal packing device that provides septal support, controls intranasal bleeding and allows nasal breathing. The expandable membrane of the packing device permits attainment of substantially uniform pressures in a nasal passageway along the splint portion and along other intranasal surfaces not contacted by the splint portion. The membrane can be of any selected shape to assure that expansion of such membrane will result in substantially continuous contact of the membrane with the splint portion and the interior nasal wall portions. If desired, the membrane can be secured directly to the splint portion or can be formed as a subassembly with the airway member. Thus, securance of the airway member to the splint portion results in simultaneous fixing of the membrane relative to the splint portion. Since the membrane expansion is directed away from the airway member the membrane does not obscure or otherwise interfere with the passage of air through the airway member. When pressurization from the membrane is no longer desired, the membrane can be deflated in a simple easy fashion and need not be removed until the entire nasal packing device 10 is removed from the nasal passage.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A nasal packing device comprising
   a. a flexible non-expandable splint portion,
   b. an air flow member joined to said flexible splint portion, said air flow member having a peripheral surface,
   c. an inflatable member comprising a flexible expandable membrane joined to the peripheral surface of said airflow member such that an inflation chamber is defined between the peripheral surface of said air flow member and said membrane said inflation chamber having a predetermined inflated condition and an uninflated condition with predetermined portions of said inflatable member being spaced from said splint portion when said inflation chamber is in said uninflated condition, and said predetermined portions of said inflatable member being expandable against said split when said inflation chamber is in said pre-determined inflated condition, and,
   d. means for directing fluid into said inflation chamber to inflate said inflation chamber.

2. A nasal packing device as claimed in claim 1 wherein said membrane is joined to the peripheral surface at selected peripheral portions of said air flow member such that said flexible membrane is expandable away from said air flow member.

3. A nasal packing device as claimed in claim 1 wherein said air flow member, in lateral cross section, is substantially circular.

4. A nasal packing device as claimed in claim 1 wherein said air flow member, in lateral cross section, is substantially C-shaped.

5. A nasal packing device as claimed in claim 1 wherein said membrane includes a portion further joined to said splint.

6. A nasal packing device as claimed in claim 1 wherein said air flow member has a proximal end portion and a distal end portion, said proximal and distal end portions being open such that an airway is defined in said air flow member from said proximal end portion to said distal end portion.

7. A nasal packing device as claimed in claim 6 wherein said means for directing fluid said inflation chamber include an inflation lumen noncommunicable with said airway.

8. A nasal packing device as claimed in claim 7 wherein said air flow member includes a wall portion and said inflation lumen is formed in said wall portion.

9. A nasal packing device as claimed in claim 1 wherein said means for directing fluid in said inflation chamber include means for inflating and deflating said chamber.

10. A nasal packing device as claimed in claim 9 wherein said inflation means include normally closed valve means for controlling the flow of fluid into or out of said inflation chamber.

11. A nasal packing device comprising
    a. a flexible non-expandable flap member having an obverse surface and a reverse surface,
    b. an elongated air flow member joined to the obverse surface of said flap member, said air flow member having a peripheral surface and opposite open end portions whereby an airway passage is defined and extends to said opposite open end portions,
    c. a flexible expandable membrane joined to the peripheral surface of said air flow member between said opposite open end portions such that an inflation chamber is defined between the peripheral surface of said air flow member and said membrane, and,
    d. means for inflating said inflation chamber such that said inflation chamber is expandable substantially around said air flow member.

12. A nasal packing device as claimed in claim 11 wherein said air flow member, in lateral cross section, is substantially circular.

13. A nasal packing device as claimed in claim 11 wherein said air flow member, in lateral cross section, is substantially C-shaped.

14. A nasal packing device as claimed in claim 11 wherein said membrane includes a portion further joined to the obverse surface of said flap member.

15. A nasal packing device as claimed in claim 11 wherein means for directing fluid in said inflation chamber include an inflation lumen noncommunicable with said airway passage.

16. A nasal packing device as claimed in claim 15 wherein said air flow member includes a wall portion and said inflation lumen is formed in said wall portion.

17. A nasal packing device as claimed in claim 11 wherein said inflation means include normally closed valve means for controlling the flow of fluid into or out of said inflation chamber.

18. A method of packing a nasal passageway comprising
   a. forming a nasal splint for the septal portion of the nose from a flexible non-expandable flap,
   b. joining an air flow member having opposite open ends and a peripheral surface to an obverse surface of the splint such that an airway passage in the air flow member extends longitudinally of the splint from one of the opposite open ends of the air flow member to the other opposite open end,
   c. securing a flexible expandable membrane to the peripheral surface of the air flow member to define an inflatable chamber between the air flow member and the membrane,
   d. providing the inflation chamber with means for directing fluid into and out of the inflation chamber to render such chamber expandable and deflatable as desired whereby the splint, the air flow member and the membrane are insertable in the nasal passageway and inflation of the inflation chamber provides a compressive force against the inner nasal wall and the splint.

19. The method of claim 18 wherein the step of providing the inflation chamber with means for directing fluid into and out of the inflation chamber includes forming an inflation lumen in a wall of the airway passage such that the inflation lumen is noncommunicable with the airway passage and communicable only with the inflation chamber.

20. The method of claim 18 including providing a normally closed control valve to communicate with the inflation lumen such that when the valve is in its closed position fluid can neither pass into or out of the chamber and when the valve is in its open position fluid can pass into and out of the inflation chamber

* * * * *